United States Patent
Franciskovich et al.

(10) Patent No.: US 8,822,174 B1
(45) Date of Patent: Sep. 2, 2014

(54) STERILIZATION INDICATOR FOR OXIDATIVE STERILANTS

(71) Applicant: American Sterilizer Company, Mentor, OH (US)

(72) Inventors: Phillip P. Franciskovich, Concord, OH (US); Tricia A. Cregger, Fairlawn, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 13/840,509

(22) Filed: Mar. 15, 2013

(51) Int. Cl.
*C12Q 1/22* (2006.01)
(52) U.S. Cl.
CPC .......................................... *C12Q 1/22* (2013.01)
USPC .............................. 435/31; 435/287.4; 422/50
(58) Field of Classification Search
None
See application file for complete search history.

(56) References Cited

U.S. PATENT DOCUMENTS

| 6,352,837 | B1 | 3/2002 | Witcher et al. |
| 2008/0070272 | A1 | 3/2008 | Franciskovich et al. |
| 2013/0273594 | A1 | 10/2013 | Ahimou et al. |

FOREIGN PATENT DOCUMENTS

| WO | 9428164 | 12/1994 |

OTHER PUBLICATIONS

Mesa Biological Indicators, MesaLabs's brochure & Information sheet, 2012, 2 pages.*
Cross et al., Applied and Environmental Microbiology, 2003, vol. 69, No. 4, p. 2245-2252.*
PCT/US2014/017916; PCT International Search Report and Written Opinion of the International Searching Authority dated May 21, 2014.

* cited by examiner

*Primary Examiner* — Kade Ariani
(74) *Attorney, Agent, or Firm* — Renner, Otto, Boisselle & Sklar, LLP

(57) ABSTRACT

A sterilization indicator for oxidative sterilants, comprising a first compartment comprising spores of one or more microorganism species, wherein the spores have been pretreated with and comprises a compound comprising a transition metal ion that is reactive with an oxidative sterilant; a second compartment comprising a growth medium and adapted to combine contents of the first compartment with contents of the second compartment for incubation after the sterilization indicator has been exposed to an oxidative sterilant; and an agent disposed in the growth medium and selected to indicate viability of the spores after the sterilization indicator has been exposed to the oxidative sterilant.

13 Claims, No Drawings

STERILIZATION INDICATOR FOR OXIDATIVE STERILANTS

TECHNICAL FIELD

The present invention relates to biological indicators for testing the efficacy of sterilization processes, more specifically, to an improved indicator for use with oxidative sterilants, which allows monitoring of the effects of the sterilant on a biological indicator further into the sterilization cycle than conventional biological indicators used with oxidative sterilants.

BACKGROUND

One of the most important classes of indicators are the biological indicators (BI). Biological indicators provide the highest degree of assurance that sterilization conditions were met throughout the processed load. This type of indicator is meant to represent the worst case for the processing system by providing within or on the indicator an extremely high number of organisms highly resistant to that particular process. Usually bacterial spores are the organism of choice for monitoring sterilization systems.

Biological indicators typically consist of microorganisms inoculated onto a carrier material. The microorganisms are typically bacterial spores that are known to be very resistant to the particular sterilization medium in which they are to be used. The carrier material can range from paper to plastic to stainless steel and may be in a variety of configurations ranging from flat surfaces to containers such as vials. Biological indicators that consist of vials and caps are known as self-contained biological indicators (SCBIs) because they contain all the elements required to process, activate and incubate the samples. The carrier is placed into a sterilization cycle along with the medical device load. Following completion of the cycle the biological indicator is incubated and monitored for growth for up to seven days. Growth of a biological indicator indicates that the sterilization process was not adequate to attain complete sterilization and that the medical device load needs to be reprocessed before use. No growth of a biological indicator confirms that conditions within the sterilizer were adequate to kill at least the number of bacterial spores loaded onto the indicator (e.g., $10^6$ bacterial spores) and therefore provides a level of assurance that the medical device load is sterile.

The resistance of biological indicators to a particular sterilization process is determined both by the spore utilized and by the configuration of the biological indicator (e.g., SCBI or SCBI in a Process Challenge Device). Therefore, to change the resistance either the sporulation method needs to be altered or a new physical configuration of the biological indicator needs to be developed. Having various sporulation methods for different biological indicators used in different sterilization processes is not desirable from a manufacturing perspective. Designing a new physical configuration for a biological indicator can get costly, for example, because new molds may be needed. Therefore, it is desirable to be able to alter the resistance of a pre-existing biological indicator in a simple manner.

Vaporous hydrogen peroxide and other oxidative sterilization processes are very effective at killing even resistant organisms such as spores. This is beneficial to hospitals, since it allows many heat sensitive medical devices to be processed through sterilizers using vaporous hydrogen peroxide (VHF) and other oxidative sterilants. However, the rapid kill that results from such oxidative sterilants makes it difficult to develop biological indicators that effectively monitor very far into the sterilization cycle. That is, because when conventional biological indicators are used in oxidative sterilant sterilization processes, the organisms in the biological indicators are so rapidly killed, it is less certain that an effective dose of the oxidative sterilant has reached and been maintained at effective levels to all portions of the load of medical devices as would be the case if the indicator were killed more slowly.

Thus, a need for a solution to the previously un-solved problem of too-rapid kill of biological indicators by oxidative sterilants has existed for some time. The present invention is intended to address this problem.

SUMMARY

The inventive concept described in this disclosure includes the use of chemical additives to the biological indicator, in which the chemical additive slows the kill kinetics of spores when exposed to oxidative sterilants such as vaporous hydrogen peroxide, ethylene oxide and ozone. In the present invention, spores are propagated and harvested as usual but before inoculating the biological indicator with the spores, the spores are resuspended (at use concentration) in a chemical solution. The chemical solution includes at least one chemical, e.g., a transition metal, that inhibits the action of oxidative sterilants such as hydrogen peroxide, ethylene oxide and ozone, or breaks down or decomposes the oxidative sterilant into non-reactive components.

For purposes of the present invention, actions of the chemical additives may include one or more of (a) inhibition of the action of the oxidative sterilant, which may include complex formation, and (b) the breakdown or decomposition of the oxidative sterilant, which may include catalytic decomposition and/or chemical neutralization reactions. These additives are generally referred to as reacting (and cognate terms such as reaction or being reactive) with the oxidative sterilant. Thus, the term "reactive with an oxidative sterilant" is deemed, for purposes of the present invention, to include any action which slows the kill kinetics of spores in the biological indicator, specifically including both inhibition of the action of and decomposition and/or neutralization of, the oxidative sterilant.

Thus, in accordance with embodiments of the present invention, there is provided a sterilization indicator for oxidative sterilants, comprising:
 a first compartment comprising spores of one or more microorganism species, wherein the spores have been pretreated with and comprises a compound comprising a transition metal ion that is reactive with an oxidative sterilant;
 a second compartment comprising a growth medium and adapted to combine contents of the first compartment with contents of the second compartment for incubation after the sterilization indicator has been exposed to an oxidative sterilant; and
 an agent disposed in the growth medium and selected to indicate viability of the spores after the sterilization indicator has been exposed to the oxidative sterilant.

In one embodiment, the one or more microorganism species comprises one or both of *Geobacillus stearothermophilus* and *Bacillus atrophaeus*, in the form of spores.

In one embodiment, the agent indicates viability of the spores by means of one or more of a color change, a turbidity change, production of fluorescence or an electrically detectable reaction.

In one embodiment, the agent is a pH indicator. In one embodiment, the pH indicator comprises Brilliant Green, Bromocresol Green, Bromocresol Purple, Bromothymol Blue, Cresol Red, Methylene Blue, Neutral Red, Phenol Red, Resazurin, or Thymol Blue.

In one embodiment, the agent is a fluorescence indicator. In one embodiment, the fluorescence indicator is a color-shifting fluorescent protein.

In one embodiment, the agent comprises at least two electrodes adapted to provide a detectable electrical signal.

In one embodiment, the agent comprises a tetrazolium salt.

In one embodiment, the transition metal ion comprises one or more of iron, copper, manganese, titanium, zinc, vanadium, silver, platinum, nickel, molybdenum, cobalt and chromium.

In one embodiment, the transition metal ion is iron in $K_3[Fe(CN)_6]$ or $Fe_7(CN)_{18}$. Potassium ferrocyanide normally has water of hydration, and may be expressed as $K_4[Fe(CN)_6].3H_2O$. It is noted that Prussian blue may also be identified by the formula $[Fe_4[Fe(CN)_6]_3]$, which is empirically the same as $Fe_7(CN)_{18}$. It is noted that the idealized formula for Prussian blue is $Fe_7(CN)_{18}$, but that Prussian blue normally has water of hydration. In one embodiment, the Prussian blue has a formula $Fe_7(CN)_{18}.xH_2O$ where x is usually 14-16. Prussian blue is normally employed as a very fine colloidal dispersion, since it is not soluble in water.

In one embodiment, the oxidative sterilant comprises one or more of hydrogen peroxide and ozone.

In one embodiment, the present invention further provides a process for determining the efficacy of a sterilization process utilizing oxidative sterilants, comprising:
  providing a sterilization indicator according to any of the preceding claims
  exposing the sterilization indicator and one or more item to be sterilized to an oxidative sterilant; and
  determining by inspection of the incubated growth medium whether the sterilization was effective.

DETAILED DESCRIPTION

Hydrogen peroxide in the vaporous state is very effective at killing microorganisms but this killing effectiveness makes it difficult to design and develop biological indicators in the traditional way that monitor a significant portion of the cycle. An effective means of increasing the inherent resistance of a biological indicator is to add a component that inhibits the action of the active sterilant or breaks the active sterilant into non-reactive components.

The concentration of the additives in solution can be varied to tune in or adjust the resistance of the biological indicator to effectively monitor more of the sterilization cycle. Biological indicators, especially in oxidative chemistries such as vaporous hydrogen peroxide, are quickly killed and will usually only monitor the very first minutes (or seconds in some conventional products) of a sterilization cycle. The present invention beneficially provides biological indicators that monitor more of the cycle than just the first few minutes or seconds of sterilization.

Oxidative chemicals can be decomposed into non-reactive components in the presence of certain reactive chemicals. For example, it has been found that vaporous hydrogen peroxide decomposes in the presence of most transition metals such as iron, copper, nickel and manganese. When materials containing these metals are processed through a vaporous hydrogen peroxide sterilizer, it has been found that the concentration of peroxide in the vicinity of these materials is decreased due to the decomposition of the hydrogen peroxide to non-reactive components. The present invention takes advantage of this finding to slow down the kill kinetics in biological indicators used to monitor oxidative sterilants, such as vaporous hydrogen peroxide.

In accordance with the present invention, transition metal reagents comprising iron, copper, nickel and manganese compounds, are used to react with oxidative sterilants to inhibit the effect of the oxidative sterilant on the biological indicator employed in the sterilization indicator used in oxidative sterilization processes. Iron compounds have been found to decompose hydrogen peroxide into non-reactive components. For example, two preferred iron compounds are potassium ferricyanide and Prussian blue. Potassium ferricyanide is soluble in water and Prussian blue, although not soluble in water, forms a fine colloidal dispersion in water.

In one embodiment of the present invention, there is provided a sterilization indicator for oxidative sterilants, including a first compartment comprising spores of one or more microorganism species, wherein the spores have been pretreated with and comprise a compound comprising a transition metal ion that is reactive with an oxidative sterilant; a second compartment comprising a growth medium and adapted to combine contents of the first compartment with contents of the second compartment for incubation after the sterilization indicator has been exposed to an oxidative sterilant; and an agent disposed in the growth medium and selected to indicate viability of the spores after the sterilization indicator has been exposed to the oxidative sterilant.

The first and second compartments may be any suitable, conventional sterilization indicator device, such as a vial with a cap adapted to hold the growth medium, and a container into which the spores can be placed. The spores may be directly placed into the container, or they may be positioned on a carrier which is then placed in the carrier. One such suitable vial is disclosed in U.S. Patent Published Application No. US 2010/0081165, which may be consulted for additional details. US 2010/0081165 is incorporated herein by reference for its teachings relating to the configuration of the vial. Another suitable sterilization indicator includes a carrier and a support, with a biological indicator supported by the carrier. One such suitable carrier and support is disclosed in U.S. Patent Published Application No. 2012/0196355, which may be consulted for additional details. US 2012/0196355 is incorporated herein by reference for its teachings relating to the configuration of the carrier, support and biological indicator. Other suitable sterilization indicators having two compartments, one containing a biological indicator and one containing a growth medium, may be suitably selected for use with the present invention by persons of skill in the art.

As noted above, in one embodiment, the one or more microorganism species comprises one or both of *Geobacillus stearothermophilus* and *Bacillus atrophaeus*, in the form of spores. These two microorganisms are commonly used in biological indicators. *Geobacillus stearothermophilus* is more commonly used with vaporous hydrogen peroxide, and *Bacillus atrophaeus* is more commonly used for ethylene oxide sterilants.

In one embodiment, the agent indicates viability of the spores by means of one or more of a color change, a turbidity change, production of fluorescence or an electrically detectable reaction. The agent may be suitably selected by the person of skill in the art. In general, the agent can be any suitable agent. The important feature of the present invention is the ability to slow down the killing of the spores, and the indicator is only to indicate the worst-case scenario when the spores have not all been killed. The following agents are considered suitable, but additional agents may be used instead, as will be understood by the skilled person.

In one embodiment, the agent is a pH indicator. In one embodiment, the pH indicator comprises Brilliant Green, Bromocresol Green, Bromocresol Purple, Bromothymol Blue, Cresol Red, Methylene Blue, Neutral Red, Phenol Red, Resazurin, or Thymol Blue. In one embodiment, the pH indicator is Bromocresol Purple, and in another embodiment, the pH indicator is Phenol Red.

In one embodiment, the agent is a fluorescence indicator. In one embodiment, the fluorescence indicator is a color-shifting fluorescent protein. Such color-shifting fluorescent proteins are known in the art. See, e.g., Macmillan, "Color-shifting fluorescent proteins highlight biology," Vanderbilt University Medical Center Reporter, 2009. See also, e.g., Subach, et al., "Monomeric fluorescent timers that change color from blue to red report on cellular trafficking", Nature Chemical Biology 5, 118-126 (2009), and Terskikh, et al., "'Fluorescent Timer': Protein That Changes Color with Time", Science, Vol. 290 no. 5496 pp. 1585-1588 (2000). Other fluorescent indicators may be suitably selected by the person of skill in the art.

In one embodiment, the agent comprises at least two electrodes adapted to provide a detectable electrical signal. The detectable electrical signal may be detected by, for example, a strip having two or more electrodes, such as disclosed in either of U.S. application Ser. No. 13/832,158, entitled COUPLED ENZYME-BASED METHOD FOR ELECTRONIC MONITORING OF BIOLOGICAL INDICATOR, filed 15 Mar. 2013, or U.S. application Ser. No. 13/836,787, entitled NON-ENZYME BASED DETECTION METHOD FOR ELECTRONIC MONITORING OF BIOLOGICAL INDICATOR, filed 15 Mar. 2013, may be suitably selected for use in detecting an electrical signal.

In one embodiment, the agent comprises a tetrazolium salt. Suitable tetrazolium salts include, for example, 3-(4,5-Dimethyl-2-thiazolyl(-2,5-diphenyl-2H-tetrazolium bromide (MTT), iodonitrotetrazolium chloride (INT), sodium 3,3,-[(Phenylamino)carbonyl]-3,4-Tetrazolium-Bis(4-methoxy-6-nitro)benzenesulfonic acid hydrate (NTT), and 4-[3-(4-Idophenyl)-2-(4-nitrophenyl)-2H-5-tetrazolio]-1,3-benzene disulfonate (WST-1). As is known in the art, cleavage of tetrazolium salts by enzymes of cells which are metabolically active lead to the formation of detectable products, such as formazan crystals. If these formazan salts are water soluble colorimetric measurements can be made directly at the end of the assay using the supernatant. If the formazan salt is not soluble in water, solubilization of the crystals must be performed before light absorbance measurements can be made. For the present invention, the water soluble formazan salts are preferred.

In one embodiment, the transition metal ion comprises one or more of iron, copper, manganese, titanium, zinc, vanadium, silver, platinum, nickel, molybdenum, cobalt and chromium. Any suitable transition metal reagent may be used. In one embodiment, the transition metal reagent is one or a combination of iron, copper, nickel or manganese compounds. Iron compounds are particularly effective for use in deactivating hydrogen peroxide. Copper compounds are effective for use in deactivating ethylene oxide. Iron and manganese compounds are effective for use in deactivating ozone. Other transition metal compounds known to react with oxidizing sterilants such as those used in the present invention may be suitably selected for use with the present invention by persons of skill in the art.

In one embodiment, the transition metal ion is iron in the form of potassium ferrocyanide, $K_3[Fe(CN)_6]$ or iron in the form of Prussian blue, $Fe_7(CN)_{18}$. Potassium ferrocyanide normally has water of hydration, and may be expressed as $K_4[Fe(CN)_6] \cdot 3H_2O$. It is noted that Prussian blue may also be identified by the formula $[Fe_4[Fe(CN)_6]_3]$, which is empirically the same as $Fe_7(CN)_{18}$. It is noted that the idealized formula for Prussian blue is $Fe_7(CN)_{18}$, but that Prussian blue normally has water of hydration. In one embodiment, the Prussian blue has a formula $Fe_7(CN)_{18} \cdot xH_2O$ where x is usually 14-16. Prussian blue is normally employed as a very fine colloidal dispersion, since it is not soluble in water.

In one embodiment, the oxidative sterilant comprises one or more of hydrogen peroxide and ozone.

In one embodiment, the present invention further provides a process for determining the efficacy of a sterilization process utilizing oxidative sterilants, comprising:
 providing a sterilization indicator according to any of the preceding claims
 exposing the sterilization indicator and one or more item to be sterilized to an oxidative sterilant; and
 determining effectiveness by subsequent growth and color change of the pH indicator.

As will be understood by the person of skill in the art, the basics of the sterilization process described herein are substantially similar to those known in the art, except for the provision of the spores of one or more microorganism species that have been pretreated with and comprises a compound comprising a transition metal ion that is reactive with an oxidative sterilant. This pretreatment of the spores provides temporary "protection" against the action of the oxidative sterilant for the purpose of "slowing down" the effect of the oxidative sterilant on the sterilization indicator, although not slowing down the effect of the oxidative sterilant on the load under treatment in the sterilization process. As noted above, the present invention is intended to provide a better estimate of the efficacy of the sterilization treatment by extending the time required to kill all the microorganism spores in the sterilization indicator, further into the sterilization process. The present invention thus is able to offset the rapidity with which the oxidative sterilants act upon conventional sterilization indicators, and thereby improve over them.

EXAMPLES

Test results using both of these chemicals in the resuspension of spores for use in biological indicators are provided in the following Examples.

Example 1

*Geobacillus stearothermophilus* Spores Resuspended in Potassium Ferricyanide

*Geobacillus stearothermophilus* spores are resuspended in potassium ferricyanide concentrations ranging from 0.5 µg/ml to 200 mg/ml in samples having a spore concentration of 1E8 per ml ($1 \times 10^8$ spores per milliliter). SCBI vials are inoculated with 20 µl (≈2 million spores) of each of the sample suspensions and air dried at least overnight. The SCBIs are then capped and run in a VHP BIER vessel for the times shown in Table 1 below using a 0.8 g injection of 59% hydrogen peroxide. Table 1 shows the grow out results for the samples tested. Comparison of the grow out results of the SCBIs containing additives with the controls demonstrates that the additives have significantly increased the resistance of the biological indicator system.

TABLE 1

Grow out results for SCBIs with potassium ferricyanide

| Sample | | Exposure Time (min.) 0.75 | 1 | 16 |
|---|---|---|---|---|
| | | Killed/Total Samples | | |
| Control (no additive) | | 20/40 | 21/38 | 19/19 |
| Potassium | 200 mg/ml | 0/10 | 0/10 | 0/10 |
| ferricyanide | 25 mg/ml | 0/10 | 0/10 | 0/10 |
| ($K_3[Fe(CN)_6]$) | 15 mg/ml | — | — | 0/10 |
| | 5 mg/ml | — | — | 0/10 |
| | 100 μg/ml | — | — | 5/10* |
| | 10 μg/ml | — | — | 9/10 |
| | 5 μg/ml | 0/10 | 3/10* | 9/10 |
| | 1 μg/ml | 0/10 | 2/10* | 8/10* |
| | 0.5 μg/ml | 0/10 | 3/10* | 7/10* |

NOTE:
*Individual values in the reported results may vary up or down slightly but an overall trend is shown that indicates that as the concentration of potassium ferricyanide used goes up, the number of survivors also goes up.

As can be seen in the data in Table 1, half or more of the indicator spores are killed in the control set in as little as 0.75 minutes, and after 16 minutes there are no survivors at all. However, with as little as 100 μg/ml of the added ferricyanide half of the exposed spores survive a full 16 minutes of exposure. Correspondingly less is required (0.5 to 5 μg/ml) to reduce the kill rate observed for the control set at 1 minute of exposure (21/38) to less than 50%. Any of the tested amounts of ferricyanide are sufficient to eliminate all spore kill at 0.75 minutes even though half are killed in the set not treated with ferricyanide.

Example 2

*Geobacillus stearothermophilus* Spores Resuspended in Prussian Blue

*Geobacillus stearothermophilus* spores are resuspended in Prussian blue concentrations ranging from 0.5 μg/ml to 123 mg/ml at a spore concentration of 1E8 per ml. SCBI vials are inoculated with 20 μl (≈2 million spores) of the appropriate suspension and air dried at least overnight. The SCBIs are then capped and run in a VHF) BIER vessel for the times listed below using a 0.8 g injection of 59% hydrogen peroxide. Table 2 shows the grow out results for the samples tested. Comparison of the grow out results of the SCBIs containing additives with the controls demonstrates that the additives significantly increase the resistance of the system.

TABLE 2

Grow out results for SOB Is with Prussian blue.

| Sample | | Exposure Time (min.) 0.75 | 1 | 16 |
|---|---|---|---|---|
| | | Killed/Total Samples | | |
| Control (no additive) | | 20/40 | 21/38 | 19/19 |
| Prussian Blue | 123 mg/ml | 0/10 | 0/10 | 0/10 |
| ($Fe_7(CN)_{18}$) | 25 mg/ml | 0/10 | 0/10 | 0/10 |
| | 15 mg/ml | — | — | 0/10 |
| | 5 mg/ml | — | — | 0/10 |
| | 100 μ g/ml | — | — | 8/10 |
| | 10 μ g/ml | — | — | 8/10 |
| | 5 μ g/ml | 0/10 | 3/10 | 7/10* |
| | 1 μ g/ml | 0/10 | 1/10* | 6/10* |
| | 0.5 μ g/ml | 0/10 | 2/10* | 10/10 |

NOTE:
*Individual values may vary up or down slightly but an overall trend is shown that indicates that as the concentration of Prussian blue used goes up, the number of survivors also goes up.

As can be seen from Table 2, comparable results are obtained for Prussian blue as compared to results obtained for potassium ferricyanide (Table 1), indicating that these iron-containing compounds are effective to retard the kill rate of vaporous hydrogen peroxide and thus extend survivability (and the ability of treated spores to monitor performance) much further into standard hydrogen peroxide cycles.

The two agents exemplified above (potassium ferricyanide and Prussian blue, although preferred, are not the only compounds that can be used to degrade oxidizing sterilants.

An important advantage of the present invention is the ability to “tune in” or “set” the resistance of a biological indicator to oxidative sterilants by changing only the concentration of the additives in the solution used to resuspend the spores. This eliminates the need for multiple sporulation methods required to achieve different spore resistance characteristics/profiles or different molds for physically changing the resistance characteristics of SCSI containers. In the present invention biocompatible chemical additives that decompose the oxidative sterilant to sub-components that are un-reactive towards spores are used in order to increase, lengthen and modify the resistance of a biological indicator. Because these modifications are concentration dependent, this provides an unprecedented control of post propagation spore crops that can be used over a broad range of oxidative sterilant cycle conditions.

While the principles of the invention have been explained in relation to certain particular embodiments, these embodiments are provided for purposes of illustration. It is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the claims.

The invention claimed is:

1. A sterilization indicator for an oxidative sterilants, comprising: a first compartment comprising spores of one or more microorganism, wherein the spores have been pretreated with and comprise a compound comprising a transition metal ion that is reactive with an oxidative sterilant, and wherein said pretreatment extends the time required to kill said spores comprising said compound comprising said reactive transition metal ion by said oxidative sterilant; a second compartment comprising a growth medium, and the indicator is adapted to combine contents of the first compartment with contents of the second compartment for incubation after the sterilization indicator has been exposed to the oxidative sterilant; and an agent disposed in the growth medium, the agent is selected to indicate viability of the spores after the sterilization indicator has been exposed to the oxidative sterilant.

2. The sterilization indicator of claim 1 wherein the microorganism comprises one or both of *Geobacillus stearothermophilus* and *Bacillus atrophaeus*.

3. The sterilization indicator of claim 1 wherein the agent indicates viability of the spores by means of one or more of a color change, a turbidity change, production of fluorescence or an electrically detectable reaction.

4. The sterilization indicator of claim 3 wherein the agent is a pH indicator.

5. The sterilization indicator of claim 4 wherein the pH indicator comprises Brilliant Green, Bromocresol Green, Bromocresol Purple, Bromothymol Blue, Cresol Red, Methylene Blue, Neutral Red, Phenol Red, Resazurin, or Thymol Blue.

6. The sterilization indicator of claim 3 wherein the agent is a fluorescence indicator.

7. The sterilization indicator of claim 6 wherein the fluorescence indicator is a color-shifting fluorescent protein.

8. The sterilization indicator of claim 3 wherein the agent comprises at least two electrodes adapted to provide a detectable electrical signal.

9. The sterilization indicator of claim 3 wherein the agent comprises a tetrazolium salt.

10. The sterilization indicator of claim 1 wherein the compound comprising a transition metal ion comprises one or more of iron, copper, manganese, titanium, zinc, vanadium, silver, platinum, nickel, molybdenum, cobalt and chromium.

11. The sterilization indicator of claim 8, wherein the transition metal ion is iron, and the compound comprising iron is $K_3[Fe(CN)_6]$ or $Fe_7(CN)_{18}$.

12. The sterilization indicator of claim 1 wherein the oxidative sterilant comprises one or more of hydrogen peroxide, ethylene oxide and ozone.

13. A process for determining the efficacy of a sterilization process utilizing an oxidative sterilants, comprising: providing the sterilization indicator according to claim 1; exposing the sterilization indicator and one or more items to be sterilized to the oxidative sterilant; and inspecting the agent disposed in the growth medium in said indicator after incubation to determine the efficacy of the sterilization process by determining the viability of said pretreated spores, wherein the agent indicates spore viability by one or more of a color change, a turbidity change, production of fluorescence or an electrically detectable reaction.

* * * * *